United States Patent [19]
Brodin et al.

[11] Patent Number: 5,912,271
[45] Date of Patent: Jun. 15, 1999

[54] PHARMACEUTICAL PREPARATION FOR PAIN MANAGEMENT

[75] Inventors: Arne Brodin, Södertälje; Anders Carlsson; Bengt Herslöf, both of Stockholm; Martin Nicklasson, Södertälje; Lisbeth Rydhag, Enhörna, all of Sweden

[73] Assignee: Astra AB, Sweden

[21] Appl. No.: 08/532,844

[22] PCT Filed: Jun. 21, 1995

[86] PCT No.: PCT/SE95/00760

§ 371 Date: Sep. 18, 1995

§ 102(e) Date: Sep. 18, 1995

[87] PCT Pub. No.: WO96/01637

PCT Pub. Date: Jan. 25, 1996

[30] Foreign Application Priority Data

Jul. 12, 1994 [SE] Sweden .................................. 9402453

[51] Int. Cl.⁶ .................... A61K 31/16; A61K 31/445; A61K 9/16; A23B 4/03
[52] U.S. Cl. ...................... 514/626; 514/330; 514/544; 514/626; 514/817; 424/489; 426/450
[58] Field of Search ..................... 514/626; 426/450; 424/489, 544, 330, 817

[56] References Cited

U.S. PATENT DOCUMENTS

| 4,610,868 | 9/1986 | Fountain et al. ........................ 424/1.1 |
| 5,635,205 | 6/1997 | Nyqvist et al. ........................ 426/450 |

FOREIGN PATENT DOCUMENTS

| 175 609 | 3/1986 | European Pat. Off. ....... A61K 47/00 |
| 455 528 | 11/1991 | European Pat. Off. ......... A61K 7/00 |
| 2 692 781 | 12/1993 | France .............................. A61K 7/02 |
| 5-163153 | 6/1994 | Japan .............................. A61K 35/30 |
| WO 88/09169 | 12/1988 | WIPO .............................. A61K 9/70 |
| WO 90/01323 | 2/1990 | WIPO .......................... A61K 31/685 |
| WO 93/19736 | 10/1993 | WIPO .............................. A61K 9/127 |
| WO 94/00127 | 1/1994 | WIPO .......................... A61K 31/575 |

OTHER PUBLICATIONS

Freeman et al., "Topical Anaesthesia of the Skin: A Review," *Pediatr. Anaesthesia* 3:129–138 (1993).

Jackson et al., "Anesthetics Alter the Lipid Composition of Barley–Root Membranes," *Planta* 162:415–421 (1984).

Matsuzaki et al., "Development of a Model Membrane System Using Stratum Corneum Lipids for Estimation of Drug Skin Permeability," *Chem. Pharm. Bull.* 41:575–579 (1993).

English language abstract of document AL1, WPI accession No. 86–071058/11, Derwent World Patents Index, Dialog file 351, 1986.

English language abstract of document AM1, WPI accession No. 91–327376/45, Derwent World Patents Index, Dialog file 351, 1991.

English language abstract of document AN1, WPI accession No. 94–036989/05, Derwent World Patents Index, Dialog file 351, 1994.

*Primary Examiner*—Keith D. MacMillan
*Attorney, Agent, or Firm*—Michael A. Sanzo; Vinson & Elkins L.L.P.

[57] ABSTRACT

A new pharmaceutical preparation comprising one or more local anaesthetic agents, a polar lipid, a triacylglycerol and optionally water. The new pharmaceutical preparation is excellent for topical treatment of pain.

18 Claims, 1 Drawing Sheet

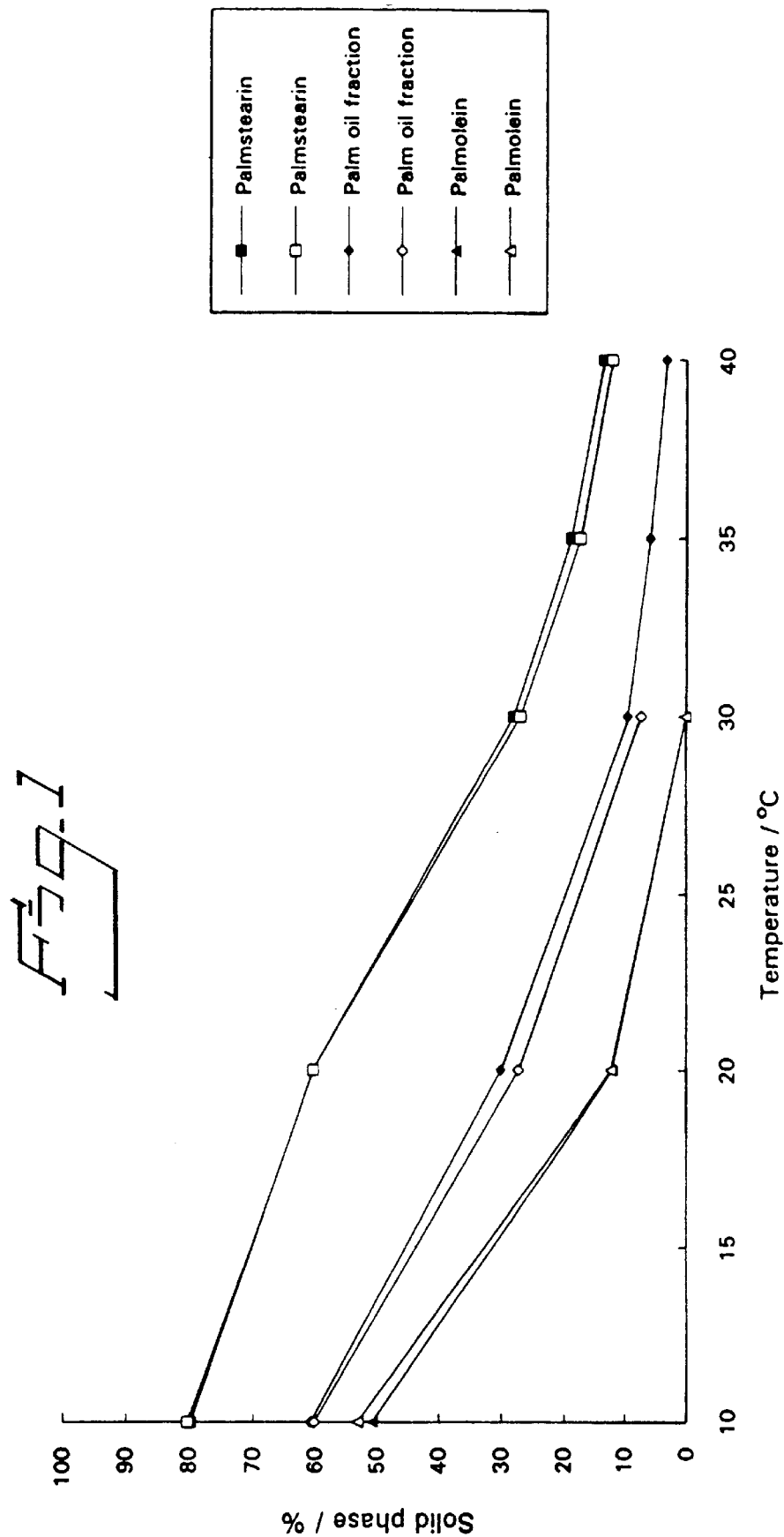

PHARMACEUTICAL PREPARATION FOR PAIN MANAGEMENT

This Application is a 371 of PCT/SE 95/00760, filed Jun. 21, 1995, which claims priority to Sweden Application No. 9402453-6, filed Jul. 12, 1994.

FIELD OF THE INVENTION

The present invention relates to a novel pharmaceutical preparation for use as a local anaesthetic for topical administration, to the use of said preparation and to a process for preparing said preparation.

BACKGROUND OF THE INVENTION

EMLA® cream is the only product on the market giving anaesthesia of intact skin. EMLA® cream is administered to the skin under occlusion for 60 minutes. In order to obtain faster onset of anaesthesia other local anaesthetic agents and vehicle systems have been tested (Refs. Freeman, et al., Pediatr. Anaesthesia 1993:3, 129). For tetracaine, an old well-known topical anaesthetic agent, there are several patent applications for different formulations, among them a cream and a patch (Refs. Woolfson and McCafferty, WO 88/09169 and Smith & Nephew, EP 0175609 respectively). WO 88/09169 discloses an onset time of approximately 30 minutes for the tetracaine cream and EP 0175609 discloses an onset time of approximately 30–45 minutes for the tetracaine patch. None of these formulations are so far on the market.

PRIOR ART

WO 93/19736 discloses a pharmaceutical composition containing a defined lipid system of at least two lipid components, at least one being amphiphatic and polar and one being non polar, and wherein the active agent is lidocaine. The problem that has been solved according to WO 93/19736 is the considerable difficulties in overcoming the poor bioabsorption of lidocaine.

WO 94/00127 discloses application of lipids and lipid formulations for the treatment of skin and mucous membrane diseases or disorders displaying epidermal hyperproliferation and disruptions of the barrier function.

EP 455528 discloses cosmetic and dermopharmaceutical. compositions containing vesicles of a mixture of phospholipids and glycolipids.

FR 2692781 discloses a cosmetic composition containing sphingomyelin from milk or fish.

JP 05163153 discloses a sphingolipid composition, solving the problem with malodour and discoloration, giving a stable composition during storage. The sphingolipid composition can be used as a cosmetic base and in the field of medicines, e.g. as emulsion. stabilisers, percutaneous promoting agents etc. The lipids are extracted from the brain.

OUTLINE OF THE INVENTION

BRIEF DESCRIPTION OF THE DRAWING

FIG. 1 is a graph showing the solid fat content in the triacylglycerol used, as determined by solid-phase NMR.

We have now surprisingly found that the problem mentioned above, namely to obtain faster onset of anaesthesia, can be solved by the new pharmaceutical preparation according to the present invention. The object of the invention is thus to provide a novel, clinically and pharmaceutically acceptable preparation for dermal pain management.

By using the pharmaceutical preparation according to the invention it is possible to achieve pain relief with a faster onset of anaesthesia than what is possible to achieve with classical topical anaesthetic agents. Another advantage with the pharmaceutical preparation according to the invention is that it is less skin irritating than topical local anaesthetic formulations according to the prior art. Still another advantage is that the hydrolysis of ester compounds such as tetracaine seem to be much slower in the lipid vehicle than in conventional formulations.

The pharmaceutical preparation according to the present invention comprises the following ingredients:

a) one or more local anaesthetic agents
b) one or more polar lipids
c) a triacylglycerol
d) optionally water The amount of the local anaesthetic is in the range 1–40%, preferably 5–10%. The amount of the polar lipid is in the range 1–40%, preferably 1–10%. The amount of the triacylglycerol is in the range 60–95%, preferably 50–85%. The amount of water is 0–95%, preferably 0–20%. All percentages are given as the percentage by weight of the total weight of the pharmaceutical preparation.

The local anaesthetic can be selected from tetracaine, lidocaine, prilocaine, mepivacaine, lidocaine/prilocaine, tetracaine/lidocaine, and other local anaesthetics and combinations thereof.

The polar lipid is preferably a sphingolipid. The sphingolipid can be ceramides, monohexosylceramides, dihexosylceramides, sphingomyelins, lysosphingomyelins, sphingosines or other suitable sphingolipids, or mixtures thereof. The polar lipid can also advantageously be a galactolipid. Preferable galactolipids are digalactosyldiacylglycerols and monogalactosylglycerols.

Preferably the sphingolipid is sphingomyelin or products derived from sphingomyelin. The sphingomyelin content is preferably established by chromatographic methods.

The sphingolipid can be extracted from mammals milk, preferably bovine milk, brain, egg yolk or erythrocytes from animal blood, preferably sheep. The sphingolipid may be synthetic or semisynthetic.

The sphingolipid being the polar lipid is related to the composition and structure of human skin lipids, specifically in the epidermis layer. Ceramides, a main lipid component of this layer, is believed to form an extracellular barrier between the cells of the epidermis. The ceramides are further believed to originate from biological processes inside the cells and may be a result of biochemical degradation of sphingomyelins or hexosylceramides. The use of a sphingolipid in the pharmaceutical preparation is therefore preferred from the point of view of biocompatibility of the preparation with the natural barrier of the epidermis.

The polar lipid can also be a galactolipid. The galactolipid can be extracted from almost any kind of glycolipid containing plant material. Preferred plant materials are seeds and kernels from grains and cereals, for instance wheat, rye, oats, corn, rice, millet and sesame. Oat groats as well as wheat gluten have a high lipid concentration and are therefore of advantage to use in the process of preparation.

The triacylglycerol used according to the present invention is preferably selected from palm oil or other natural oils with a similar solid fat content or melting range. When palm oil is selected, commercial palm oil is fractionated to specific mixtures of suitable triacylglycerols, based on the combination of mainly palmitic, oleic and stearic esters of glycerol respectively. It is important for the triacylglycerol mixture utilized in the pharmaceutical preparation to be very pure and free from other glycerides, such as mono- and diacylglycerols. Such purity is preferably confirmed by established chromatographic methods, for example thinlayer chromatography or high-performance liquid chromatography. It is further important that the triacylglycerol mixture fulfils the bulk quality requirements for use in pharmaceutical preparations. Such requirements are for example oxidation status and content of free fatty acids. The triacylglycerol may also be synthetic or semisynthetic.

The triacylglycerol fractions are defined by the percentage solid fat content, determined by solid-phase NMR as described in IUPAC method no. 2150, 7th edition. Thus, in the temperature range 25–35° C. the fractions should contain 0–50% (w/w) solid fat, preferably 0–30% (w/w), see FIG. 1.

The pharmaceutical preparation according to the invention is administered topically, and can be administered in form of an ointment, a cream or included in a patch.

Pharmaceutical preparations

The pharmaceutical preparations according to the present invention were prepared by melting the triacylglycerol in an open water bath at a temperature range of 40–70° C. Thereafter the local anaesthetic and the polar lipid were weighed in a vial. The triacylglycerol was melted and transferred to the vial and the mixture was dispersed with an Ystral homogenizer at approximately 1000 rpm and at a temperature range of 40–70° C. for 2–4 minutes. The amount of water required to form a topically applicable formulation was added at room temperature and the formulation was mixed carefully.

The following examples describe in detail the pharmaceutical preparations according to the invention.

The sphingolipids used in examples 1–7 and 11 were sphingolipids purified from bovine milk containing 60–80% sphingomyelins. The sphingolipids used in example 10 were sphingolipids purified from egg yolk, containing approximately 98% sphingomyelin. The galactolipid used in example 9 was purified from oats.

EXAMPLE 1

Tetracaine 5%
Sphingolipids from milk 14.3%
Palm oil fraction 80.7%

EXAMPLE 2

Tetracaine 25%
Sphingolipids from milk 4%
Palmolein 70%
Water 1%

EXAMPLE 3

Tetracaine 25%
Sphingolipids from milk 3%
Palmolein 52%
Water 20%

EXAMPLE 4

Tetracaine 25%
Sphingolipids from milk 4%
Palmstearin 70%
Water 1%

EXAMPLE 5

Tetracaine 25%
Sphingolipids from milk 3%
Palmstearin 52%
Water 20%

EXAMPLE 6

Tetracaine 10%
Sphingolipids from milk 1%
Palmstearin 69%
Water 20%

EXAMPLE 7

Tetracaine 10%
Sphingolipids from milk 10%
Palmolein 79%
Water 1%

EXAMPLE 8

Tetracaine 5%
Palm oil fraction 95%

EXAMPLE 9

Tetracaine 25%
Galactolipids 22%
Palmstearin 33%
Water 20%

EXAMPLE 10

Tetracaine 5%
Sphingolipids from egg yolk 14.3%
Palm oil fraction 80.7%

EXAMPLE 11

Tetracaine 25%
Sphingolipids from milk 22%
Palmstearin 33%
Water 20%

Biological studies

Topical anaesthesia/analgesia during occlusion of intact skin in the guinea-pig was studied with lipid formulations of local anaesthetics, as a modification of the method originally described by Edith Bulbring and Isabella Wajda in J Pharmacol Exp Ther 1945: 85: 78–84.

Male guinea-pigs (Dunkin-Hartley strain), weight range of 300–400 g, were used. The hair was removed from the back of the animal with a depilatory (Opilca® Hans Schwarzkopf GmbH, Hamburg, Germany). The hairless and smooth skin was washed with. soap and water and the animal was kept in a cage under a desk lamp about two hours before experimentation. On pricking the back of the animal with a cannula (22G) (Kifa (with no point)) or a von Frey filament (4.74) (Semmes-Weinstein pressure aesthesiometer), a twitching of the skin was elicited. A circular piece of gauze (one up to eight layers) saturated with test formulation in a thin plastic cup (4.5 cm$^2$) was applied to the middle of the back. The cup was then covered with Self-adhesive (Fixomull® BDF Beiersdorf AG Hamburg, Germany) and the occlusion was finally protected with an elastic bandage. At the end of the application period the treated area was wiped with a tissue and then examined for signs of local irritation. The skin which had been in contact with the formulation was pricked with a cannula or a von Frey filament under constant pressure six times at different places and the presence or absence of the twitching response in the skin of treated area was noted. This procedure was repeated at regular intervals of five minutes.

The number of pricks not eliciting a response gave an indication of the degree of sensory anaesthesia or analgesia. Groups of two, three or six animals were used for each test formulation.

Results

For all formulations discussed below, the percentage of anaesthesia/analgesia was measured after 15 minutes of contact time under occlusion in the guinea-pig.

In spite of the short contact time, 15 minutes, a waterfree formulation of 5% of the active drug, tetracaine in sphingolipids and palm oil gave approximately 80% of anaesthesia/analgesia with a duration of more than 90 minutes (Example 1).

When compared to a similar formulation of 5% of tetracaine in palm oil without sphingolipids; the percentage of anaesthesia/analgesia was approximately 40% and the duration was less than 30 minutes (Example 8). From these examples it is obvious that the presence of sphingolipids reduce the onset time and extend the duration of anaesthesia/analgesia.

Further increasing the concentration of tetracaine to 10% in the presence of sphingolipids, a more saturated triacylglycerol fraction, palmstearin and 20% of water, resulted in 100% of anaesthesia/analgesia with a long duration (Example 6).

Further increasing the content of tetracaine to 25% and sphingolipids to 3% in palmstearin, also resulted in a high percentage of anaesthesia/analgesia (Example 4). Addition of 20% of water to the pharmaceutical preparation according to Example 4, resulted in 100% of anaesthesia/analgesia with a long duration. To optimize the effect of the drug, the saturation of the triacylglycerol fraction and the water content of the formulation were important parameters.

Using a more well-defined sphingolipid from egg yolk containing approximately 98% of sphingomyelins did not alter the effect of the active drug dramatically (Example 10). The sphingolipids used in the other examples were all extracted from bovine milk, containing approximately 60–80% sphingomyelins. The difference between sphingolipids from bovine milk and egg yolk is obviously not a critical parameter for the effect of the active drug.

A comparison between formulations containing either sphingolipids or galactolipids gave approximately the same percentage of anaesthesia/analgesia at a constant amount of the active drug. The function of the polar lipids is dual, meaning that the polar lipids reduce the onset time and extend the duration of anaesthesia/analgesia, and are also acting as dispersing agent or stabilizer of the formulation.

The best mode of performing the invention is at present considered to be the pharmaceutical preparation according to Example 6.

Conclusion

The polar lipids have at least two functions in formulations intended for dermal pain management. They reduce the onset time and extend the duration of anaesthesia, as well as being non-irritating. They are also efficient stabilizers or dispersing agents for pharmaceutical formulations intended for dermal anaesthesia.

We claim:

1. A pharmaceutical preparation comprising:
   (a) 1–40% of one or more local anaesthetic agents;
   (b) 1–40% of one or more polar lipids selected from the group consisting of sphingolipids or galactolipisd;
   (c) 60–95% of a triacylglycerol; and
   (d) 0–95% water;
   and wherein the percentages are the percentages by weight of the total weight of the pharmaceutical preparation.

2. A pharmaceutical preparation according to claim 1, wherein the polar lipid is a sphingolipid.

3. A pharmaceutical preparation according to claim 1, wherein the polar lipid is a galactolipid.

4. A pharmaceutical preparation according to claim 1, wherein the polar lipids are a mixture of sphingolipids and galactolipids.

5. A pharmaceutical preparation according to claim 2, wherein the sphingolipid is a sphingolipid mixture with at least 1% sphingomyelin.

6. A pharmaceutical preparation according to claim 3, wherein the galactolipid is a galactolipid mixture with at least 1% digalactosyldiacylglycerol.

7. A pharmaceutical preparation according to claim 1, wherein the trigacylglycerol is defined by the percentage solid fat content, determined by solid-phase NMR in the temperature range 25–35° C.

8. A pharmaceutical preparation according to claim 7, wherein the triacylglycerol is a palm oil fraction.

9. A pharmaceutical preparation according to claim 7, wherein the triacylglycerol is palmolein.

10. A pharmaceutical preparation according to claim 7, wherein the triacylglycerol is palmstearin.

11. A pharmaceutical preparation according to claim 1, wherein the amount of the local anaesthetic is 5–10%, the amount of the polar lipid is 1–10%, the amount of the triacylglycerol is 60–85% and the amount of water is 0–20%.

12. A pharmaceutical preparation according to claim 1, containing

Tetracaine 10%

Sphingolipids from bovine milk 1%

Palmstearin 69%

Water 20%.

13. A pharmaceutical preparation according to claim 1, wherein said preparation is in form of an ointment or a cream.

14. A pharmaceutical preparation according to claim 1, wherein said preparation is incorporated in a patch.

15. A process for the preparation of a pharmaceutical preparation according to claim 1, wherein the triacylglycerol is melted at a temperature of 40–70° C. one or more local anaesthetic agents and one or more polar lipids are weighed in a vial, the melted triacylglycerol is added and transferred to the vial, the mixture is dispersed with a homogenizer at 40–70° C. for 2–4 minutes and the amount of water required to form a topically applicable formulation is added and mixed.

16. A method of treating a patient for pain comprising, applying the composition of claim 1 to said patient in an amount sufficient to reduce or eliminate said pain.

17. The method of claim 16, wherein said composition is applied to the skin of said patient to achieve local anesthesia.

18. The method of claim 16, wherein said composition is in the form of an ointment, cream or patch.

* * * * *